United States Patent
Abe

(10) Patent No.: US 7,929,666 B2
(45) Date of Patent: Apr. 19, 2011

(54) X-RAY IMAGING SYSTEM, CONTROL METHOD THEREFOR, CONTROL PROGRAM, AND X-RAY IMAGING APPARATUS

(75) Inventor: Masahiro Abe, Yokohama (JP)

(73) Assignee: Canon Kabushiki Kaisha, Tokyo (JP)

(*) Notice: Subject to any disclaimer, the term of this patent is extended or adjusted under 35 U.S.C. 154(b) by 136 days.

(21) Appl. No.: 11/697,834

(22) Filed: Apr. 9, 2007

(65) Prior Publication Data

US 2007/0253534 A1    Nov. 1, 2007

(30) Foreign Application Priority Data

Apr. 12, 2006  (JP) .................. 2006-110102

(51) Int. Cl.
H05G 1/58    (2006.01)
(52) U.S. Cl. ...................... 378/116; 378/115
(58) Field of Classification Search ............ 378/115–116
See application file for complete search history.

(56) References Cited

U.S. PATENT DOCUMENTS

| | | | |
|---|---|---|---|
| 2003/0030004 A1* | 2/2003 | Dixon et al. | 250/370.09 |
| 2005/0169425 A1* | 8/2005 | Takasawa | 378/97 |
| 2007/0116180 A1* | 5/2007 | Omernick et al. | 378/116 |
| 2007/0297569 A1* | 12/2007 | Saunders | 378/108 |

FOREIGN PATENT DOCUMENTS

| | | |
|---|---|---|
| JP | 11-009579 | 1/1999 |
| JP | 2000-350718 | 12/2000 |

* cited by examiner

*Primary Examiner* — Hoon Song
(74) *Attorney, Agent, or Firm* — Canon USA Inc. IP Division

(57) ABSTRACT

There is provided an X-ray imaging system to which an X-ray sensing unit including a solid-state imaging device having sensitivity to X-rays interchangeably connects. The system includes an X-ray generation unit which applies X-rays to the X-ray sensing unit, and an imaging controller which controls the X-ray sensing unit and the X-ray generation unit. The system also includes a sensing unit information receiver which receives sensing unit information from the X-ray sensing unit. The system further includes a control parameter setting unit which automatically sets control parameters for the imaging controller on the basis of the sensing unit information received by the sensing unit information receiver.

13 Claims, 11 Drawing Sheets

401

NO VALID SENSING UNIT IS ATTACHED

402

SENSING UNIT IS DETECTED.
SETTINGS ARE BEING UPDATED.
PLEASE WAIT FOR A WHILE.

403

IMAGING PARAMETER SETTING

SENSING UNIT NAME : CXDI2005

[CHEST PA]

| kV | 130 |
| mA | 80 |
| msec | 50 |
| mAs | 4 |

CANCEL    OK

404

IMAGING PARAMETER SETTING

SENSING UNIT NAME : CXDI2010

[CHEST PA]

| kV | 100 |
| mA | 50 |
| msec | 20 |
| mAs | 1 |

CANCEL    OK

X-RAY IMAGING SYSTEM, CONTROL METHOD THEREFOR, CONTROL PROGRAM, AND X-RAY IMAGING APPARATUS

BACKGROUND OF THE INVENTION

1. Field of the Invention

The present invention relates to an X-ray imaging system, a control method therefor, a control program, and An X-ray imaging apparatus.

2. Description of the Related Art

Currently, there have been available various examination apparatuses using X-rays in the medical field, for example, a plain orbital X-ray imaging apparatus, a CT apparatus (computerized tomography scanner), and a fluoroscopic apparatus (C-arm or the like), and "image diagnosis" using images obtained from these examination apparatuses has been actively practiced. These X-ray imaging apparatuses have recently begun to use solid-state imaging devices (flat panel detectors) as X-ray sensing units, which have begun to replace conventional imaging systems using films and I.I.s (image intensifiers).

Currently practiced radiography has no concept of imaging while changing an X-ray sensing unit as needed. For example, although I.I.s of various sizes are available in fluoroscopic imaging using C-arms, there is no practice of imaging while changing the I.I. in accordance with the imaging operation to be performed. This is because an I.I. is heavy and very poor in portability. However, use of low-profile, light-weight flat panel detectors makes it possible to easily change an X-ray sensing unit in accordance with the imaging operation to be performed. For example, patent reference (Japanese Patent Laid-Open No. 2000-350718) discloses a method of imaging by selectively using a plurality of sensing units. As described above, in imaging operation requiring fluoroscopy of only the heart, imaging by using a sensing unit with a small size allows an operator to easily handle the unit during surgical operation. This can therefore provide an environment which allows the operator to easily perform surgical operation.

When the operator changes a sensing unit and operates to image, a controller needs to perform proper control in accordance with the X-ray sensing unit to be attached. That is, it is necessary to change the settings in the controller in accordance with the attached sensing unit. In addition, when the operator replaces the currently used sensing unit with another unit having a different size and exhibiting an improvement in function, it is necessary to replace the controller itself with another controller. This imposes a high cost burden on the user. In addition, installation of such controllers requires a lot of time and labor.

SUMMARY OF THE INVENTION

The present invention allows realization of an X-ray imaging system and X-ray imaging apparatus to perform a control suitable for X-ray sensing unit attached therewith.

According to one aspect of the present invention, the foregoing problem is solved by providing an X-ray imaging system which allows interchangeable connection of an X-ray sensing unit, comprising an X-ray generation unit adapted to apply X-rays to the X-ray sensing unit, an imaging controller adapted to control the X-ray sensing unit and the X-ray generation unit, a receiver adapted to receive sensing unit information from the X-ray sensing unit and a parameter setting unit adapted to set a control parameter for the imaging controller on the basis of the sensing unit information received by the receiver to receive sensing unit information.

According to another aspect of the present invention, the foregoing problem is solved by providing an X-ray imaging system which allows interchangeable connection of an X-ray sensing unit, comprising an X-ray generation unit adapted to apply X-rays to the X-ray sensing unit, an imaging controller adapted to control the X-ray sensing unit and the X-ray generation unit, a driver module receiver placed in the X-ray sensing unit and adapted to receive a driver module for controlling a function of the X-ray sensing unit from the X-ray sensing unit, and an imaging controller updating unit adapted to update the imaging controller by using the driver module received by the driver module receiver.

According to still another aspect of the present invention, the foregoing problem is solved by providing an X-ray imaging system which allows interchangeable connection of an X-ray sensing unit, comprising an X-ray generation unit adapted to apply X-rays to the X-ray sensing unit, an imaging controller adapted to control the X-ray sensing unit and the X-ray generation unit, a driver module receiver adapted to receive a driver module for controlling a function of the X-ray sensing unit from an external network, and an imaging controller updating unit adapted to update the imaging controller by using the driver module received by the driver module receiver.

According to yet another aspect of the present invention, the foregoing problem is solved by providing an X-ray imaging apparatus which allows interchangeable connection of an X-ray sensing unit, comprising an imaging controller adapted to control the X-ray sensing unit, a sensing unit information receiver adapted to receive sensing unit information from the X-ray sensing unit, and a parameter setting unit adapted to set a control parameter for the imaging controller on the basis of the sensing unit information received by the sensing unit information receiver.

According to still yet another aspect of the present invention, the foregoing problem is solved by providing an X-ray imaging apparatus which allows interchangeable connection of an X-ray sensing unit, comprising an imaging controller adapted to control the X-ray sensing unit, a driver module receiver placed in the X-ray sensing unit and adapted to receive a driver module for controlling a function of the X-ray sensing unit from the X-ray sensing unit and an imaging controller updating unit adapted to update the imaging controller by using the driver module received by the driver module receiver.

According to yet still another aspect of the present invention, the foregoing problem is solved by providing an X-ray imaging apparatus which allows interchangeable connection of an X-ray sensing unit, comprising an imaging controller adapted to control the X-ray sensing unit, a driver module receiver adapted to receive a driver module for controlling a function of the X-ray sensing unit from an external network, and an imaging controller updating unit adapted to update the imaging controller by using the driver module received by the driver module receiver.

According to still yet another aspect of the present invention, the foregoing problem is solved by providing a control method for an X-ray imaging system which allows interchangeable connection of an X-ray sensing unit, comprising the steps of receiving sensing unit information from the connected X-ray sensing unit; and setting a control parameter for an imaging controller on the basis of the sensing unit information received in the step of receiving the sensing unit information.

According to yet still another aspect of the present invention, the foregoing problem is solved by providing a control method for an X-ray imaging system which allows interchangeable connection of an X-ray sensing unit and includes an imaging controller, comprising the steps of receiving a driver module for controlling a function of the X-ray sensing unit from the X-ray sensing unit, and updating the imaging controller by using the driver module received in the step of receiving the driver module.

According to still yet another aspect of the present invention, the foregoing problem is solved by providing a control method for an X-ray imaging system which allows interchangeable connection of an X-ray sensing unit and includes an imaging controller, comprising the steps of receiving a driver module for controlling a function of the X-ray sensing unit from an external network, and updating the imaging controller by using the driver module received in the step of receiving the driver module.

According to yet still another aspect of the present invention, the foregoing problem is solved by providing a control program for an X-ray imaging system which allows interchangeable connection of an X-ray sensing unit and includes an imaging controller, the program causing the X-ray imaging system to execute the steps of receiving sensing unit information from the connected X-ray sensing unit and setting a control parameter for the imaging controller on the basis of the sensing unit information received in the step of receiving the sensing unit information.

According to still yet another aspect of the present invention, the foregoing problem is solved by providing a control program for an X-ray imaging system which allows interchangeable connection of an X-ray sensing unit and includes an imaging controller, the program causing the X-ray imaging system to execute the steps of receiving a driver module for controlling a function of the X-ray sensing unit from the X-ray sensing unit, and updating the imaging controller by using the driver module received in the step of receiving the driver module.

According to yet still another aspect of the present invention, the foregoing problem is solved by providing a control program for an X-ray imaging system which allows interchangeable connection of an X-ray sensing unit and includes an imaging controller, the program causing the X-ray imaging system to execute the steps of receiving a driver module for controlling a function of the X-ray sensing unit from an external network, and updating the imaging controller by using the driver module received in the step of receiving the driver module.

Further features of the present invention will be apparent from the following description of exemplary embodiments with reference to the attached drawings.

DESCRIPTION OF THE EMBODIMENTS

Preferred embodiments of the present invention will now be described in detail with reference to the drawings. It should be noted that the relative arrangement of the components, the numerical expressions and numerical values set forth in these embodiments do not limit the scope of the present invention unless it is specifically stated otherwise.

First Embodiment

Figure 1:
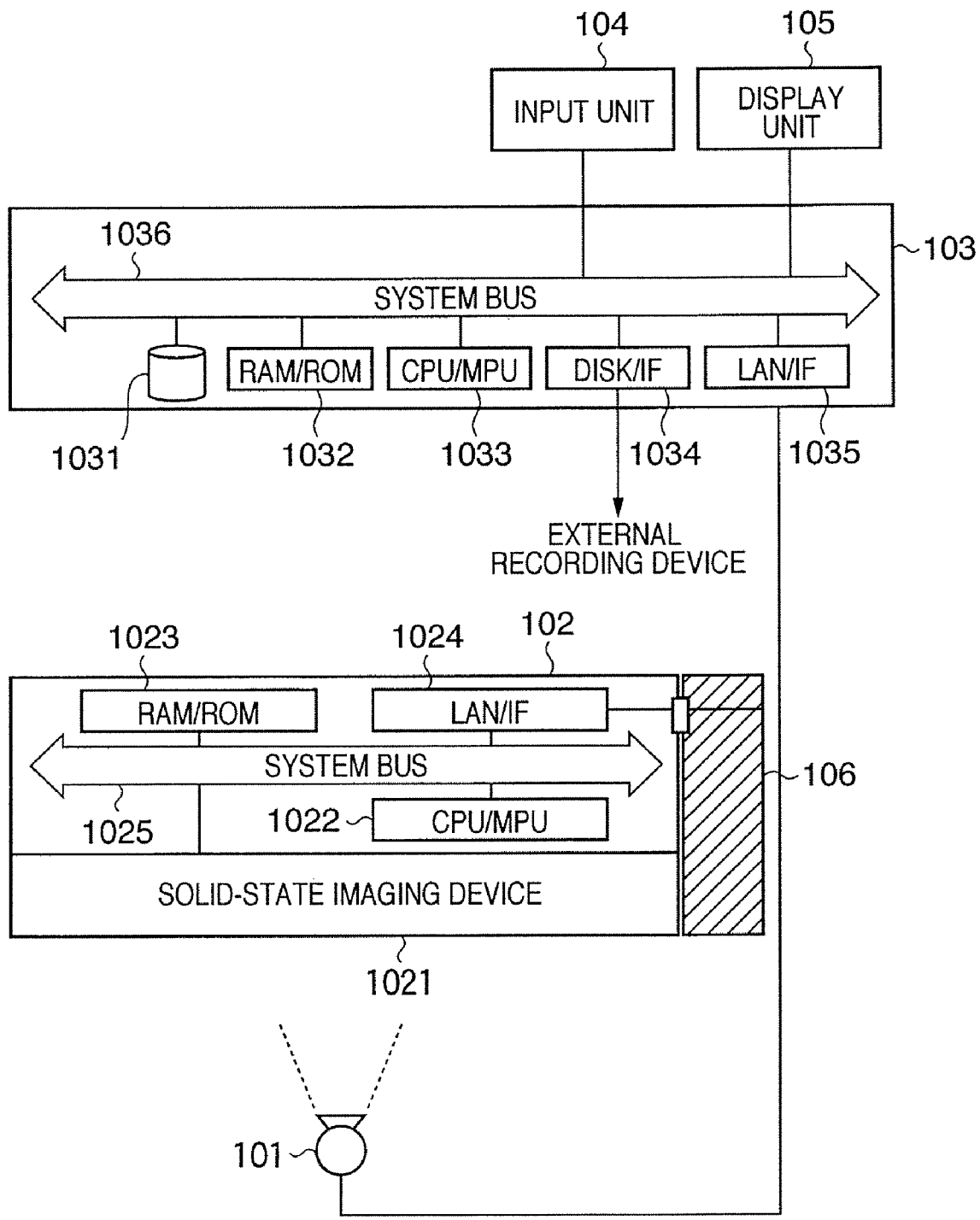
FIG. 1 is a block diagram showing a hardware configuration according to the first embodiment.

FIG. 1 is a block diagram for explaining the hardware configuration of an X-ray imaging system according to this embodiment. Reference numeral 101 denotes an X-ray generator which generates X-rays; and 102, an X-ray sensing unit which receives X-rays emitted from the X-ray generator 101 and converts the X-rays into an image signal. The X-ray sensing unit 102 includes a solid-state imaging device 1021 which receives an X-ray signal and converts it into an electrical signal, and a CPU/MPU 1022 which is an arithmetic processing apparatus for performing control in the sensing unit. The X-ray sensing unit 102 includes a RAM/ROM 1023 which is a storage device such as a RAM (Random Access Memory) or a ROM (Read Only Memory). The X-ray sensing unit 102 also includes a communication interface LAN/IF 1024 for exchanging image data and control signals with an imaging controller 103. In the X-ray sensing unit 102, these components connect to each other through a system bus 1025.

The imaging controller 103 controls this imaging system. The imaging controller 103 has a nonvolatile storage device 1031 such as a hard disk, a storage device RAM/ROM 1032, and a CPU/MPU 1033 which performs various kinds of arithmetic processing. The imaging controller 103 has a DISK/IF 1034 for writing data in an external portable medium or a recording device. The imaging controller 103 also includes a communication interface LAN/IF 1035 for exchanging control signals and image data with the X-ray generator 101 and the X-ray sensing unit 102. In the imaging controller 103, these components connect to each other through a system bus 1036.

An input unit 104 such as a mouse, keyboard, foot pedal, or hard button with which the user performs various input operations and a display unit 105 such as a CRT or an LCD by which the user checks setting contents and image data connect to the imaging controller 103. Reference numeral 106 denotes an X-ray sensing unit attaching/detaching unit which allows the X-ray sensing unit 102 to be attached/detached. When the X-ray sensing unit 102 connects to the X-ray sensing unit attaching/detaching unit 106, it electrically connects to the imaging controller 103.

Figure 2:
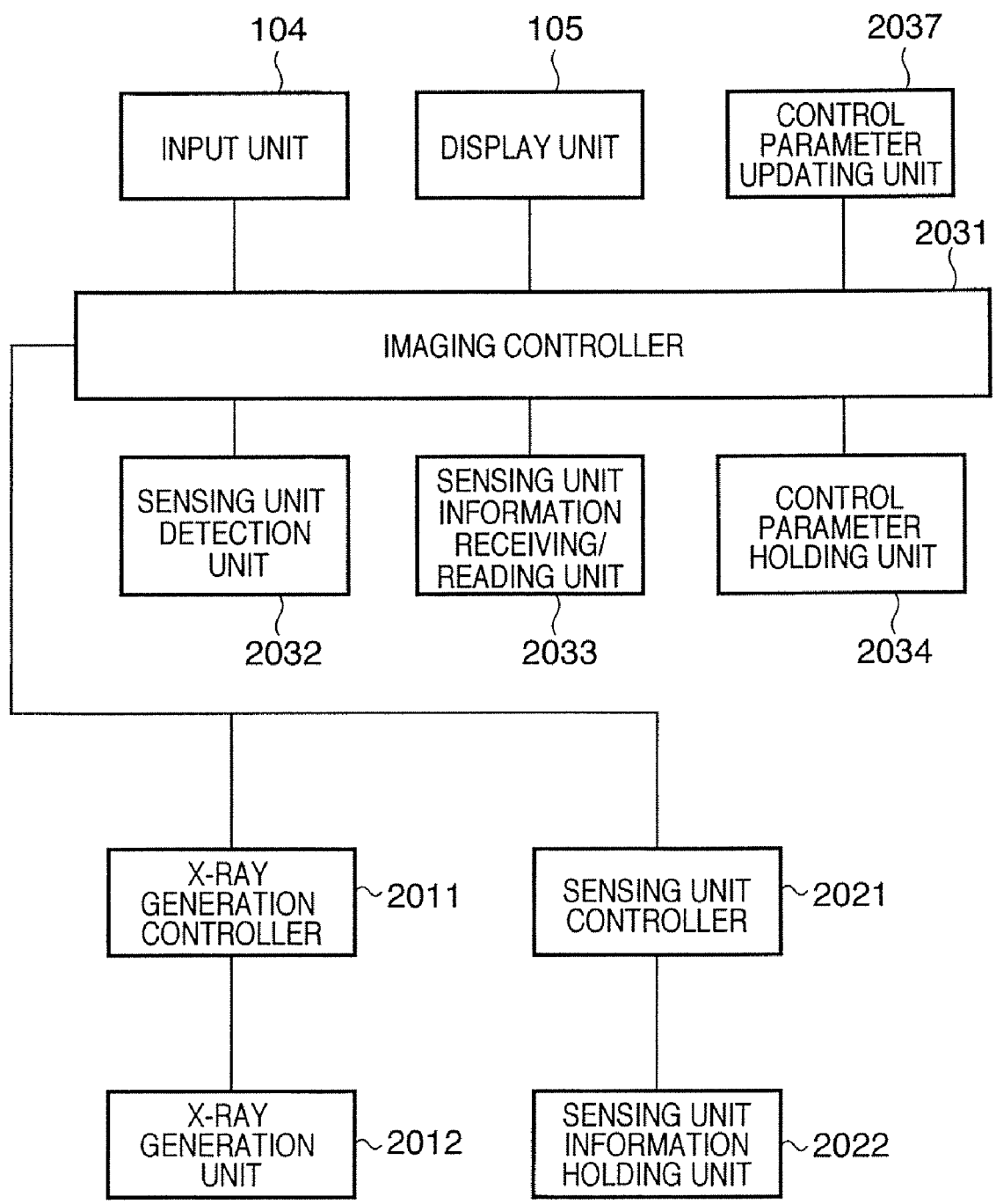
FIG. 2 is a block diagram showing a functional configuration according to the first embodiment.

The functional configuration of this embodiment will be described next with reference to FIG. 2. FIG. 2 is a block diagram showing the functional configuration of this imaging system. As described with reference to FIG. 1, the imaging system mainly comprises three components, for example, the X-ray generator 101, X-ray sensing unit 102, and imaging controller 103. Reference numeral 2021 denotes a sensing unit controller which controls the X-ray sensing unit 102, drives the X-ray sensor, and performs processing such as image processing and data transfer; 2031, an imaging controller which controls imaging by the imaging controller 103, and performs various kinds of processing associated with imaging, for example, control signal transfer to the X-ray sensing unit, data reception, control signal transfer to the X-ray generation unit, and data transfer to an external network; and 2011, an X-ray generation controller which controls an X-ray generation unit 2012, and performs various kinds of control operations associated with the generation of X-rays, for example, changing the radiation quality or dose of X-rays and changing the aperture value of a collimator based on a control signal received from the imaging controller 2031.

A sensing unit detection unit 2032 is a function for detecting the X-ray sensing unit 102 attached to the X-ray sensing unit attaching/detaching unit 106. The imaging controller 103 executes this function. The X-ray sensing unit 102 has a sensing unit information holding unit 2022 which holds its own sensing unit information, and holds the device information (e.g., the sensor size, sensitivity, and maximum frame rate) of the X-ray sensing unit. Reference numeral 2033 denotes a sensing unit information receiving/reading unit which receives and reads the sensing unit information held by the sensing unit information holding unit 2022.

Reference numeral 2034 denotes a control parameter holding unit which holds various control parameters associated with radiography. In this case, control parameters include imaging parameters such as a tube voltage, tube current, and mAs value, image processing parameters, an X-ray collimator aperture value, a frame rate at the time of fluoroscopic imaging, and a continuous fluoroscopy time. Control parameters also include general imaging conditions and control parameters associated with radiography, for example, an X-ray-tube-to-sensor distance, tube position, C-arm position, and anatomical program. Reference numeral 2037 denotes a control parameter updating unit. The control parameter updating unit 2037 updates control parameters held in the control parameter holding unit 2034 based on sensing unit information received and analyzed by the sensing unit information receiving/reading unit 2033. As described with reference to FIG. 1, the input unit 104 is a function by which the user inputs information to the imaging controller 103.

The X-ray generation unit 2012 is a function which the tube of the X-ray generator 101 has. Although this embodiment has exemplified the case wherein one X-ray sensing unit is attached to the system, the number of X-ray sensing units which can be attached to the system is not limited to one. For example, the embodiment may have a plurality of X-ray sensing unit attaching/detaching units to allow a plurality of X-ray sensing units to be attached to the system.

Figure 3:
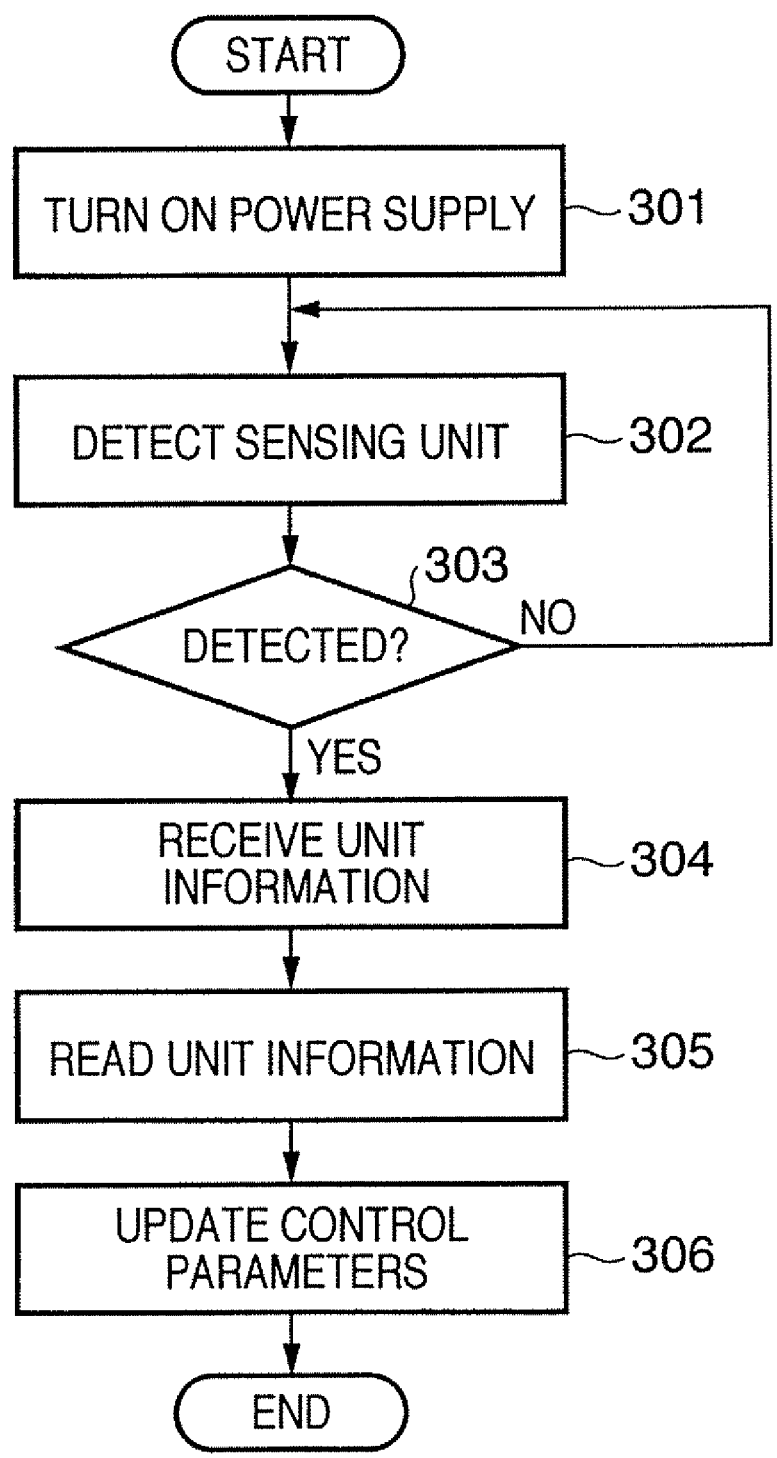
FIG. 3 is a flowchart showing a procedure between the instant when the power supply is turned on and the instant when an imaging ready state is set according to the first embodiment.

A sequence of operation in this embodiment will be described next with reference to FIG. 3. FIG. 3 is a flowchart by which this X-ray imaging system updates the state of the imaging controller to an optimal state in the interval between the instant when the operator turns on the power supply of the X-ray imaging system and the instant when the system is set in an imaging ready state. In step 301, the operator turns on the power supply of this X-ray imaging system. After the operator turns on the power supply in step 301, the X-ray imaging system detects in step 302 whether an X-ray sensing unit is attached to the sensing unit attaching/detaching unit. If it is determined in step 303 that an X-ray sensing unit is detected in step 302, the process advances to step 304. If the result is NO in step 303, the process returns to step 302. In step 304, the sensing unit information receiving/reading unit 2033 starts to receive the X-ray sensing unit information held in the sensing unit information holding unit 2022. Upon completion of this reception, the process advances to step 305. In step 305, the sensing unit information receiving/reading unit 2033 reads the sensing unit information received in step 304. In step 306, the control parameter updating unit 2037 optimally updates control parameters associated with imaging by the imaging controller 103 based on the unit information read in step 305. Upon completion of step 306, the control parameters are properly set to allow the X-ray imaging system to start imaging.

Figure 4:
FIG. 4 is a view showing an example of a GUI (Graphical User Interface) according to the first embodiment.

An example of a GUI (Graphic User Interface) displayed on the display unit 105 when control parameters are updated upon detection of an X-ray sensing unit will be described next with reference to FIG. 4. FIG. 4 shows an example of the GUI displayed on the display unit of this X-ray imaging system. If the X-ray sensing unit 102 is not attached to the X-ray sensing unit attaching/detaching unit 106, the display unit 105 of the imaging controller 103 displays a window for indicating that no valid X-ray sensing unit is attached to the system, as indicated by reference numeral 401. When the X-ray sensing unit 102 is attached to the X-ray sensing unit attaching/detaching unit 106, the display unit 105 displays a message notifying that a sensor is detected, as indicated by reference numeral 402. The imaging controller 103 then receives the sensing unit information, and notifies the operator of information prompting him/her to wait until control parameters are updated.

Upon completion of updating of control parameters, this message window disappears, and the operator can use this X-ray imaging system. Reference numerals 403 and 404 show how a GUI changes when a given X-ray sensing unit is replaced by another X-ray sensing unit. Reference numeral 403 denotes a setting GUI for imaging parameters in a sensing unit of a model called CXDI 2005 as an X-ray sensing unit name, and reference numeral 404 denotes a setting GUI for imaging parameters in a sensing unit of a model called CXDI 2010 as an X-ray sensing unit name. Assume that the CXDI 2010 is a model higher in the sensitivity of the solid-state imaging device than the CXDI 2005, and can image with an X-ray dose smaller than that in the prior art. As indicated by reference numerals 403 and 404, imaging parameters are automatically set so as to image with a smaller dose, only by replacing the sensor.

Although this embodiment has exemplified imaging parameters, control parameters to be automatically updated are not limited to imaging parameters. That is, control parameters include control parameters associated with radiography, for example, image processing parameters, an X-ray collimator aperture value, a frame rate at the time of fluoroscopic imaging, a continuous fluoroscopy time, an X-ray-tube-to-sensor distance, a tube position, a C-arm position, and an anatomical program. That is, any control parameters associated with radiography can be set regardless of the types of parameters.

Figure 5:
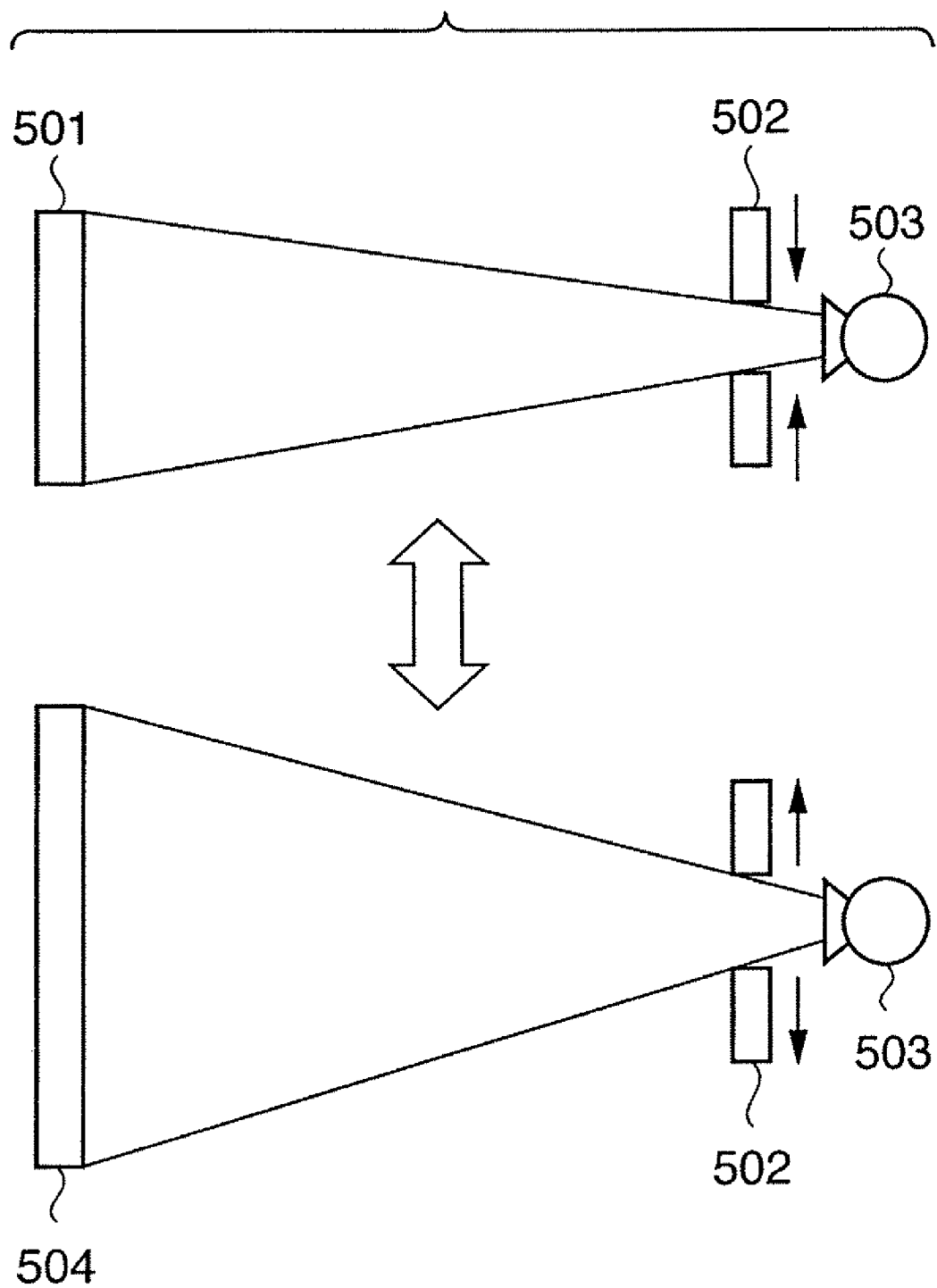
FIG. 5 is a view showing automatic adjustment for a collimator according to the first embodiment.

FIG. 5 is a conceptual view showing that the aperture value of an X-ray collimator 502 is automatically set upon sensing unit replacement in this X-ray imaging system. The X-ray collimator 502 narrows an X-ray application region. Reference numeral 503 denotes an X-ray tube serving as an X-ray source. An X-ray sensing unit 501 differs in sensor surface size from an X-ray sensing unit 504. The X-ray sensing unit 504 has a larger light-receiving surface than the X-ray sensing unit 501. When the operator detaches the X-ray sensing unit 501 from the X-ray sensing unit attaching/detaching unit 106 and attaches the X-ray sensing unit 504, the imaging controller 103 receives sensing unit information and automatically sets control parameters, as described above. As a result, as shown in FIG. 5, an aperture value is automatically set to match the aperture width of the X-ray collimator 502 with the sensor size of the X-ray sensing unit 504 to be used.

As described above, according to the X-ray imaging system of this embodiment, the imaging controller is automatically set in accordance with the apparatus information of the X-ray sensing unit to be used. This eliminates the necessity to manually set control parameters every time the user changes a sensing unit, thereby providing an imaging system which improves the flexibility of the system and provides convenience for the operator.

Second Embodiment

The second embodiment of the present invention will be described next. The above first embodiment has exemplified the imaging system which simply automatically sets parameter information of a newly attached X-ray sensing unit. In contrast to this, the second embodiment will exemplify a system which can also automatically update an imaging controller when the user replaces a currently used unit with an X-ray sensing unit having a new function.

When the user replaces an X-ray sensing unit with an X-ray sensing unit having a new function, the system requires a new driver module which a conventional imaging controller 103 does not hold. This is, for example, a case wherein the user replaces an X-ray sensing unit which can capture only still images with an X-ray sensing unit having both the functions of performing still image capturing and moving image capturing (fluoroscopy). In this case, a driver module is a program which is compiled to control An X-ray imaging apparatus. In this case, only automatically setting control parameters does not allow use of the new moving image capturing function. This embodiment will therefore exemplify a case wherein the imaging controller receives the driver module which the X-ray sensing unit holds, and the module is automatically incorporated into the system, thereby simply updating the system and easily setting a state to allow the use of the new function.

Figure 6:
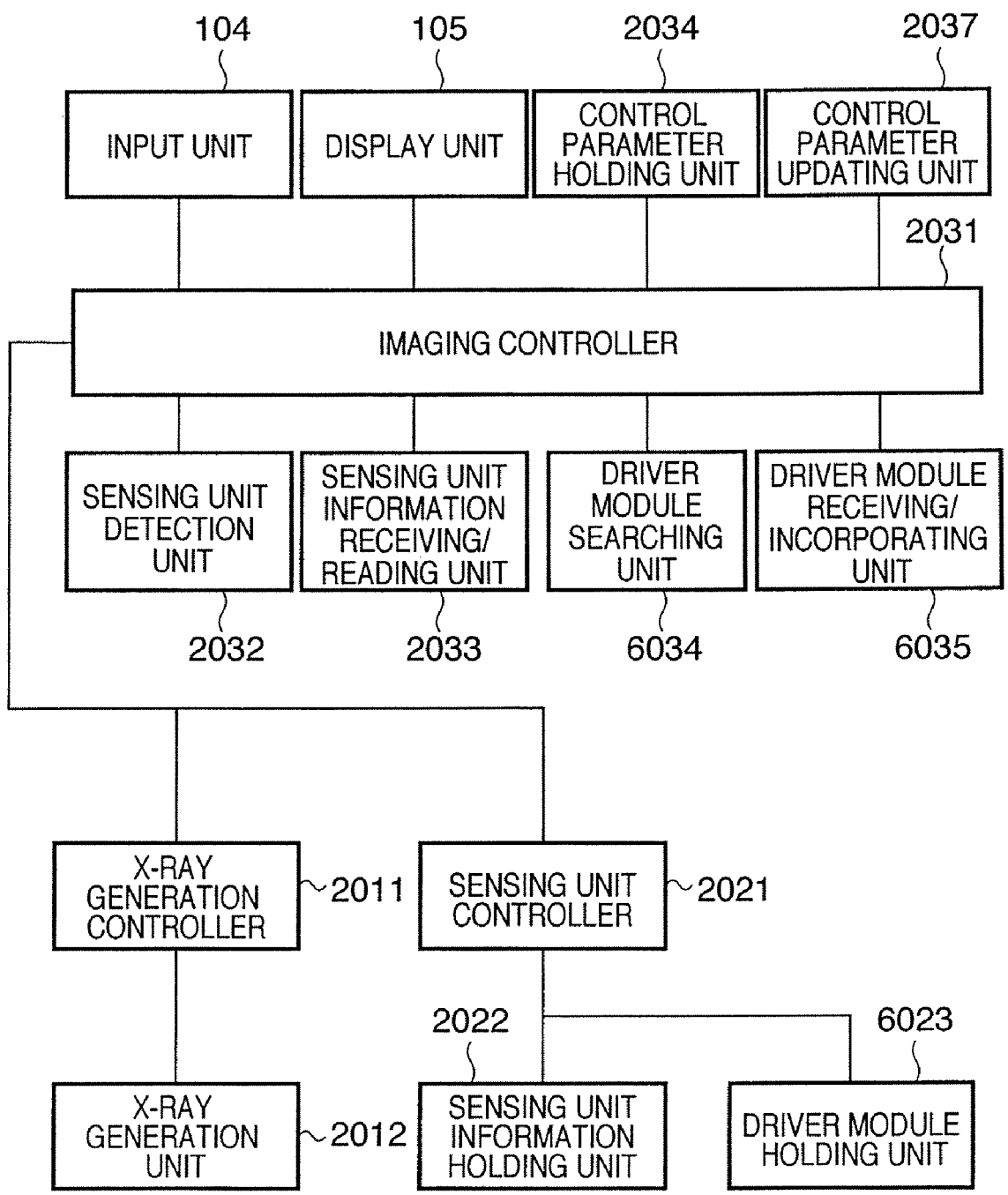
FIG. 6 is a block diagram showing a functional configuration according to the second embodiment.

Note that a hardware configuration in this embodiment is the same as that in the first embodiment. FIG. 6 is a block diagram showing the functional configuration of the embodiment. The same reference numerals as in FIG. 2 denote the same functional components in FIG. 6, and a description thereof will be omitted.

A driver module holding unit 6023 is incorporated into an X-ray sensing unit 102, and holds a driver module for the sensing unit itself. A driver module searching unit 6034 searches the imaging controller 103 for a driver module suitable for the currently attached X-ray sensing unit.

In addition, a driver module receiving/incorporating unit 6035 has a function of receiving the driver module for the X-ray sensing unit which is held by the driver module holding unit 6023, and incorporating the module into the imaging controller 103.

Figure 7:
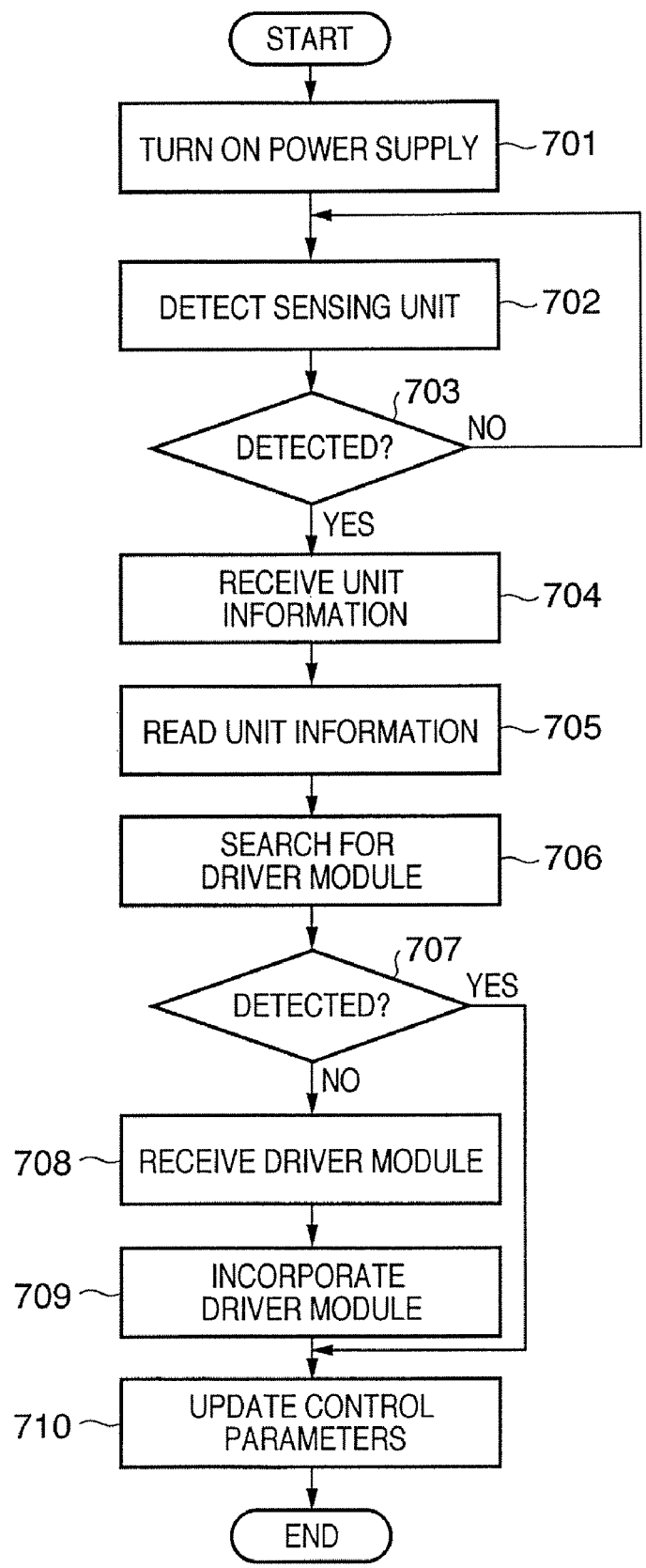
FIG. 7 is a flowchart showing a procedure between the instant when the power is turned on and the instant when an imaging ready state is set according to the second embodiment.

A sequence of operation in this embodiment will be described next with reference to FIG. 7. FIG. 7 is a flowchart in which the imaging controller 103 receives a driver module for the currently attached X-ray sensing unit 102 and updates the driver for the X-ray sensing unit 102 in the interval between the instant when the operator turns on the power supply of the X-ray imaging system and the instant when the system is set in an imaging ready state. In step 701, the operator turns on the power supply of the X-ray imaging system. After the operator turns on the power supply in step 701, the X-ray imaging system detects in step 702 whether the X-ray sensing unit 102 is attached to An X-ray sensing unit attaching/detaching unit 106.

If it is determined in step 703 that an X-ray sensing unit is detected in step 702, the process advances to step 704. If the result is NO in step 703, the process returns to step 702. In step 704, a sensing unit information receiving/reading unit 2033 receives the X-ray sensing unit information held in a sensing unit information holding unit 2022. Upon completion of reception, the process advances to step 705. In step 705, the sensing unit information receiving/reading unit 2033 reads the sensing unit information received in step 704. In step 706, the driver module searching unit 6034 searches the imaging controller 103 for a driver module most suitable for the X-ray sensing unit.

If the driver module searching unit 6034 searches out a driver module in step 706, the process shifts from step 707 to step 710. If the driver module searching unit 6034 could not search out any driver module, the process shifts to step 708. In step 708, the driver module for the X-ray sensing unit which is held in the driver module holding unit 6023 is received. In step 709, the driver module received in step 708 is incorporated in the imaging controller 103. Note that the driver module receiving/incorporating unit 6035 performs steps 708 and 709. In step 710, a control parameter updating unit 2037 optimally updates control parameters associated with imaging by the imaging controller 103 based on the unit information read in step 705. Upon completion of step 710, the imaging controller properly incorporates the driver module for the X-ray sensing unit, and sets control parameters. In this state, the imaging system can start imaging.

Figure 8:
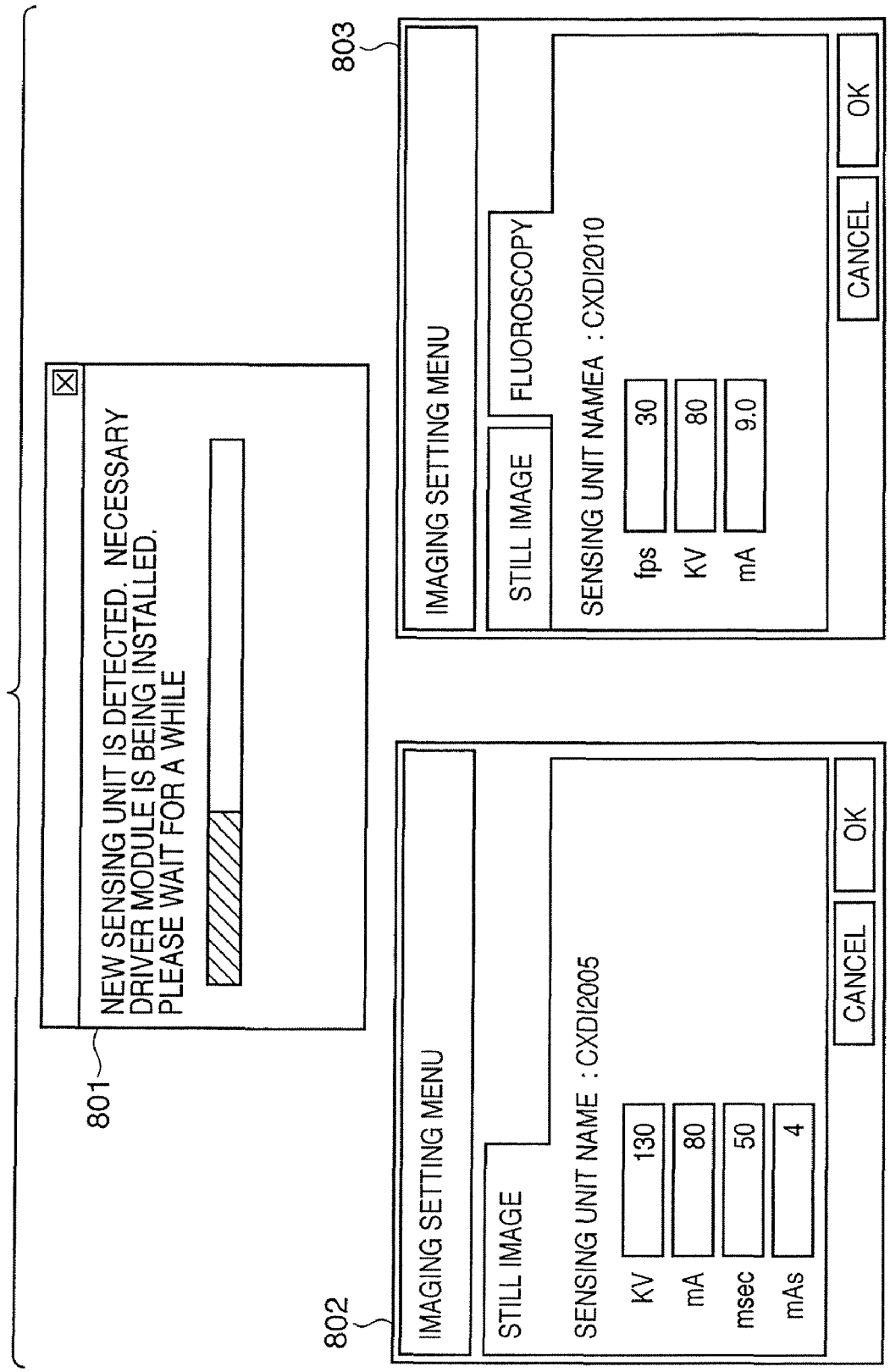
FIG. 8 is a view showing an example of a GUI (Graphical User Interface) according to the second embodiment.

FIG. 8 shows an example of a GUI (Graphic User Interface) displayed on the display unit 105 when a driver module is received from an X-ray sensing unit upon detection of the X-ray sensing unit, and the system is updated. FIG. 8 shows an example of the GUI displayed on the display unit of this X-ray imaging system. If a new X-ray sensing unit is attached to the system, and no driver module for controlling the sensing unit exists in the imaging controller 103, for example, a window 801 for indicating that the system has been updated is displayed. When the system incorporates a driver module, the system stops displaying this message window, and the operator can use the X-ray imaging system.

Reference numerals 802 and 803 show how the GUI changes when the operator replaces a given X-ray sensing unit with another X-ray sensing unit. Reference numeral 802 denotes a GUI to be displayed when a model exclusively designed for still image capturing, which is a model called CXDI 2005 as an X-ray sensing unit name, is attached to the system, and reference numeral 803 denotes a GUI to be displayed when a sensor of a model called a CXDI 2010 as an X-ray sensing unit name is attached to the system. This sensing unit is a model capable of performing moving image capturing (fluoroscopy) in addition to still image capturing. As is obvious from the GUIs 802 and 803, when the operator changes the X-ray sensing unit, a necessary driver module is incorporated into the imaging controller 103, and a setting tab for fluoroscopic imaging is added to the control GUI.

In addition, as described in the first embodiment, control parameters are automatically set based on sensing unit information. Obviously, when the operator changes the X-ray sensing unit to the CXDI 2005 again, the fluoroscopy tab disappears from the control GUI, and the GUI 802 is restored. At this time, the driver module for the CXDI 2010 is not deleted from the system but is stored in the imaging controller 103. When the CXDI 2010 connects to the system again, use of the held driver module makes it possible to optimize the control system.

According to this embodiment, when the operator attaches an X-ray sensing unit having a new function to the system, the X-ray sensing unit transfers a control module necessary for the controller to automatically update the controller. This allows the operator to easily use the new function without manually updating the imaging controller.

Third Embodiment

The third embodiment of the present invention will be described below. According to the second embodiment, an X-ray sensing unit holds a driver module for the X-ray sensing unit. In contrast to this, the third embodiment will exemplify a case wherein another apparatus on an external network holds a driver module. For example, a driver module receiving/incorporating unit 6035 can download and incorporate a driver module placed on a specific site on the Internet. This makes it possible, when a defect is found in a driver module which has been incorporated into a given sensing unit and shipped out, to easily incorporate a correction module for the system by receiving the latest driver module. In this case, the driver module held in the X-ray sensing unit is compared with the driver module placed on the WEB site to incorporate the more suitable one of the driver modules.

Figure 9:
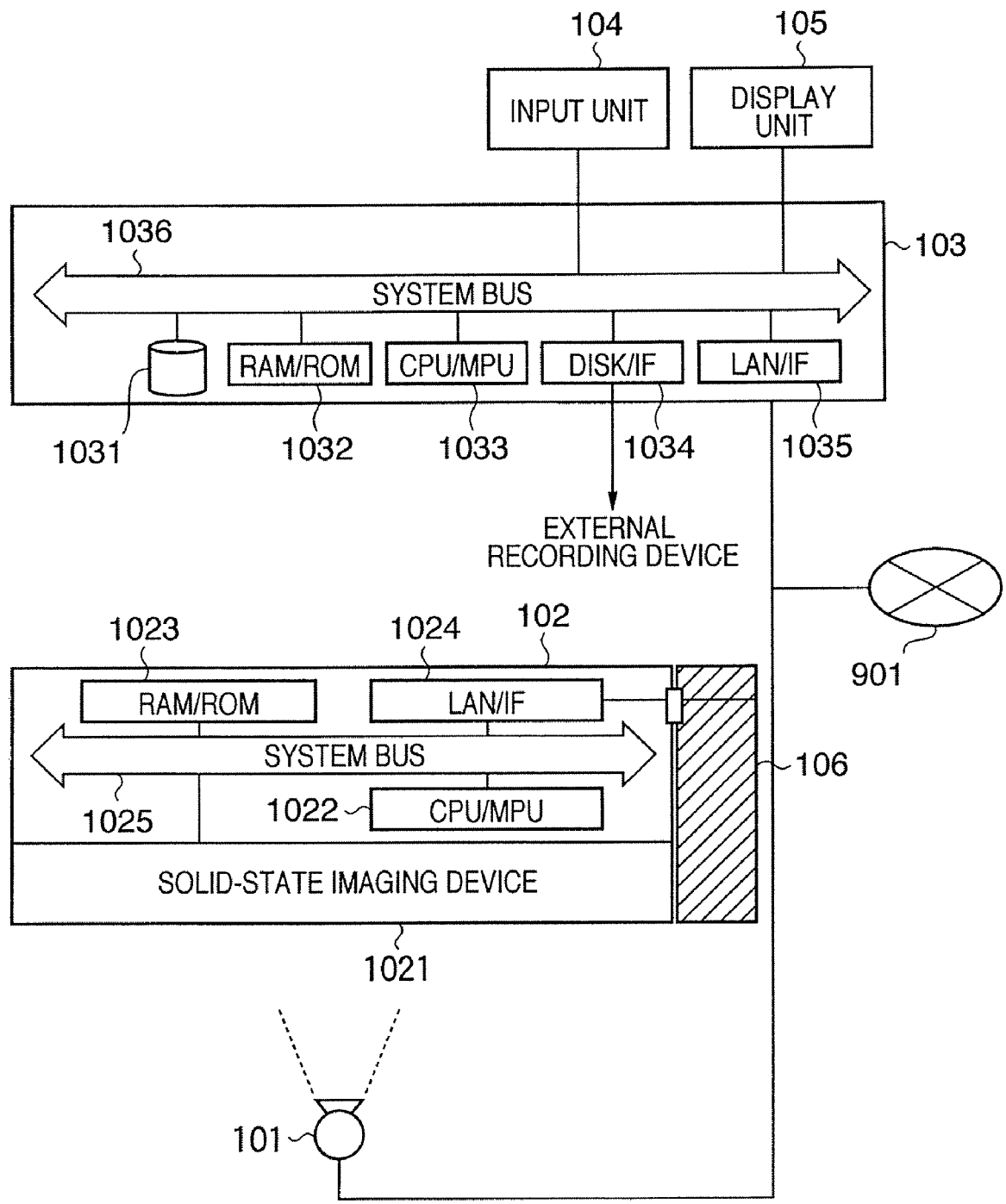
FIG. 9 is a block diagram showing a hardware configuration according to the third embodiment.
Figure 10:
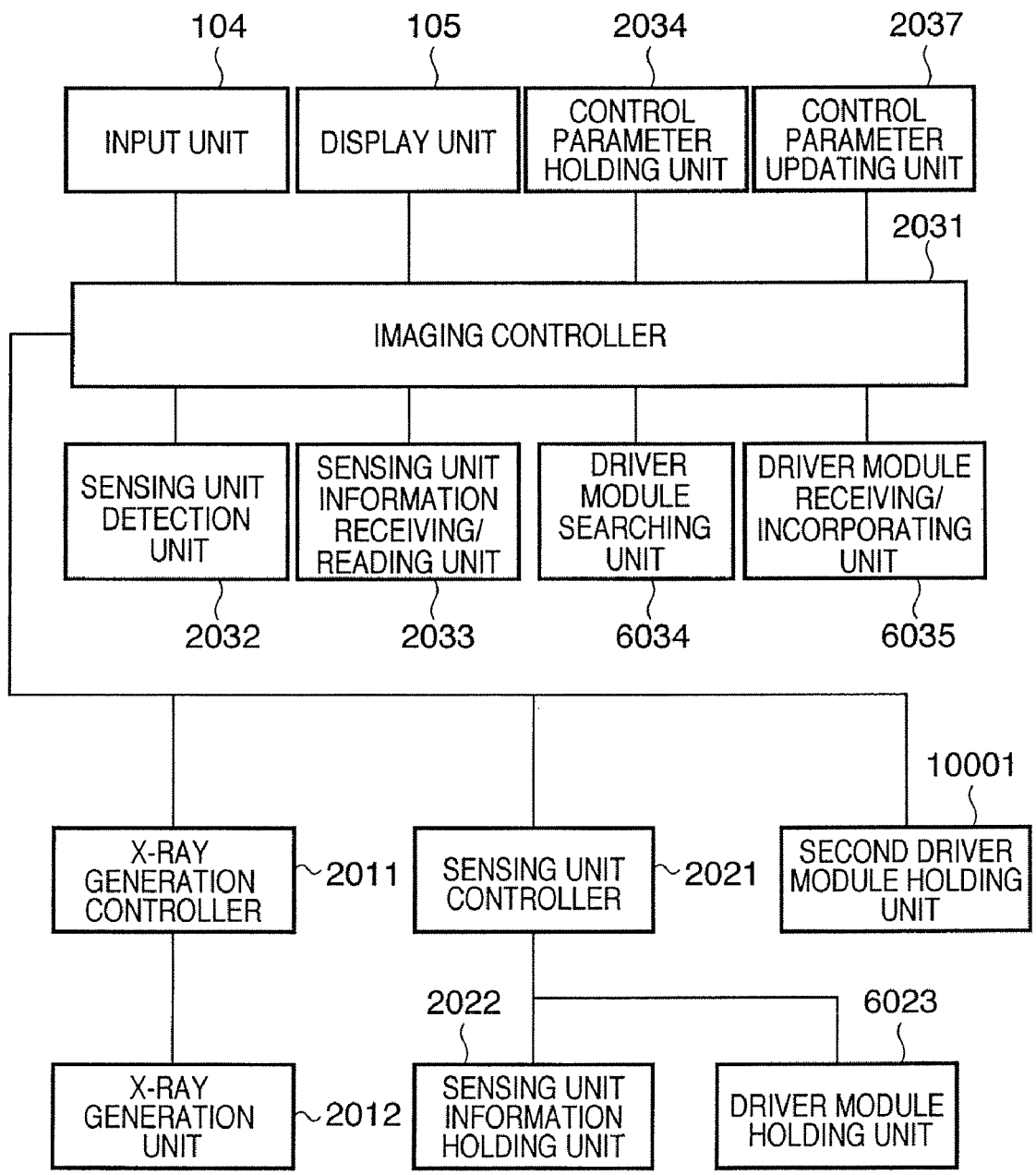
FIG. 10 is a block diagram showing a functional configuration according to the third embodiment.

FIG. 9 shows a hardware configuration in this embodiment. This configuration is obtained by adding an external network (Internet) 901 to the hardware configuration in FIG. 1. FIG. 10 is a block diagram showing the functional configuration of the embodiment. The functional configuration in FIG. 10 is obtained by adding a second driver module holding unit 10001 to the functional configuration in FIG. 6. The second driver module holding unit 10001 is placed on the external network 901. This is equivalent to holding the driver module in a site on the Internet, as described above.

Figure 11:
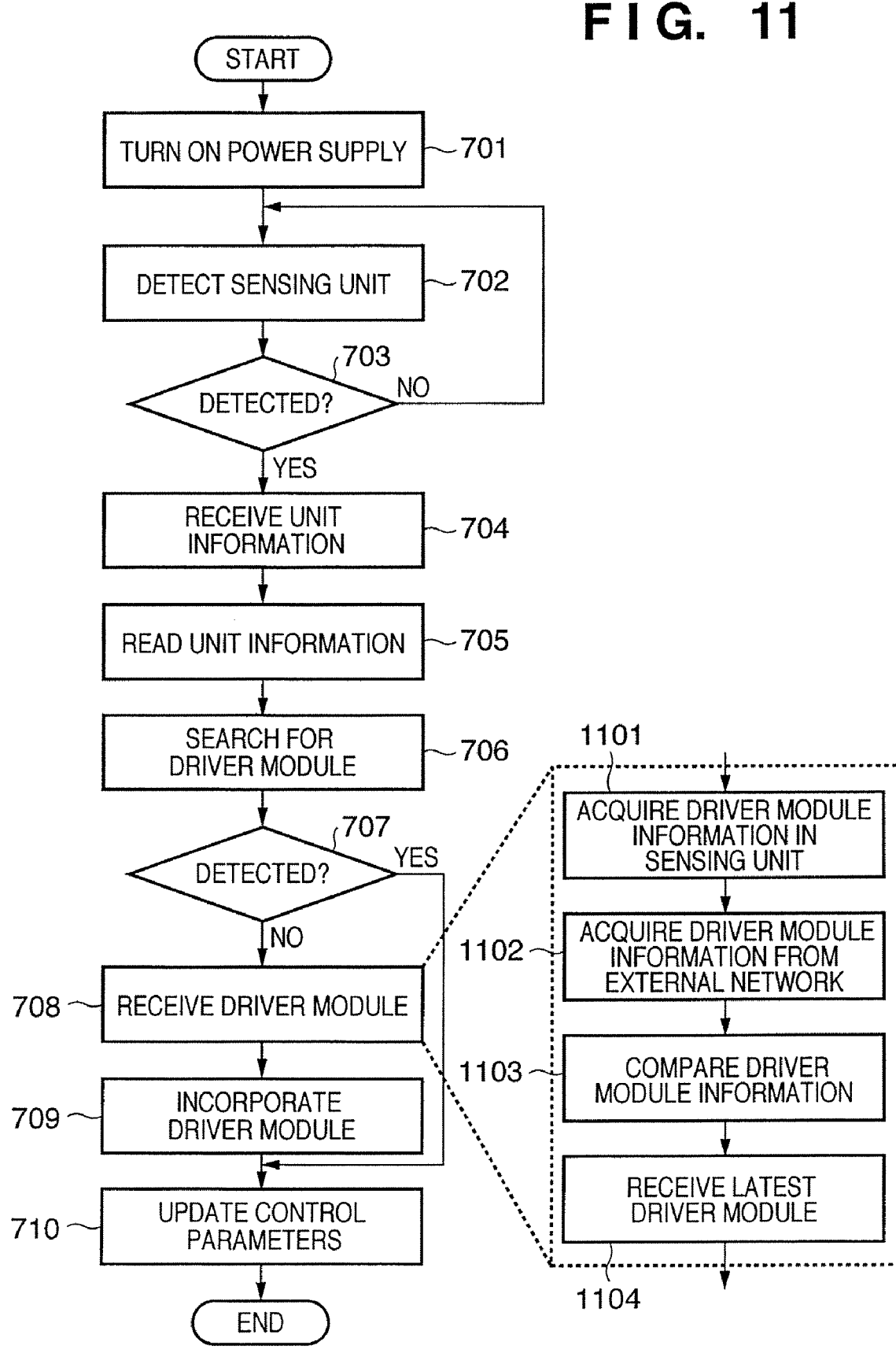
FIG. 11 is a flowchart showing a procedure between the instant when the power is turned on and the instant when an imaging ready state is set according to the third embodiment.

FIG. 11 is a flowchart in which an imaging controller receives a driver module for an attached X-ray sensing unit and is updated in the interval between the instant when the operator turns on the power supply of this X-ray imaging system and the instant when the system is set in an imaging ready state. This flowchart is basically the same as that shown in FIG. 7 except that step 708 in FIG. 7 is replaced by steps 1101 to 1104 in FIG. 11. Since the operation up to step 708 is the same as that in the flowchart of FIG. 7, the steps which replace step 708 will be described in this embodiment. Note that as in the second embodiment, the driver module receiving/incorporating unit 6035 performs the processing from step 1101 to step 1104. Step 1101 is the step of acquiring the information of a driver module in a sensing unit. More specifically, this is the step of acquiring the module name and version number of the driver module.

In step 1102, the driver module receiving/incorporating unit 6035 acquires the module name and version number of a driver module placed on an external network. In step 1103, the driver module receiving/incorporating unit 6035 determines an optimal driver module by comparing the driver module placed in the sensing unit, whose information is acquired in step 1101, with the driver module placed on the external network, whose information is acquired in step 1102. That is, in step 1103, the driver module receiving/incorporating unit 6035 selects the latest version number. In step 1104, the driver module receiving/incorporating unit 6035 receives the driver module selected in step 1103 from the X-ray sensing unit or the external network. The subsequent processing is the same as that in FIG. 7, and hence a description thereof will be omitted.

According to the above flowchart, first of all, after an X-ray sensing unit is searched for a driver module, a search is made for a driver module on an external network. However, this embodiment is not limited to this. It suffices to search for a drive module only on the external network without searching the X-ray sensing unit.

As described above, according to the X-ray imaging system of this embodiment, even if, for example, a defect is found in a driver module incorporated in an X-ray sensing unit, an optimal driver module is automatically downloaded from the Internet and incorporated in the imaging controller 103. This saves the operator from having to manually perform upgrading operation.

Fourth Embodiment

Mounting a wireless interface on an X-ray sensing unit can implement an X-ray imaging system without including an X-ray sensing unit attaching/detaching unit 106. In this case, as is obvious, attaching an X-ray sensing unit 102 to the sensing unit attaching/detaching unit is equivalent to electrically connecting the X-ray sensing unit 102 to an imaging controller 103.

Other Embodiment

Although embodiments have been described in detail above, the present invention can be applied to a system comprising a plurality of devices, or to an apparatus comprising a single device.

The present invention can be implemented by directly or remotely supplying programs for implementing the functions of the embodiments described above to a system or apparatus and causing the system or apparatus to read out and execute the programs. Therefore, the technical range of the present invention incorporates the program codes themselves which are installed in a computer to allow the computer to implement the functions/processing of the present invention.

In this case, each program may take any form, for example, an object code, a program executed by an interpreter, and script data supplied to an OS, as long as it has the function of the program.

As a recording medium for supplying the programs, a floppy (registered trademark) disk, hard disk, optical disk, magnetooptical disk, MO, CD-ROM, CD-R, CD-RW, magnetic tape, nonvolatile memory card, ROM, DVD (DVD-ROM or DVD-R), or the like can be used.

In addition, methods of using the programs include the following. A client PC connects to an Internet site by using the browser of the PC to download each program of the present invention itself or a file containing an automatic install function into a recording medium such as a hard disk. Alternatively, the programs can be supplied by dividing the program codes constituting each program of the present invention into a plurality of files, and downloading the respective files from different homepages. That is, the present invention also incorporates a WWW server which allows a plurality of users to download program files for causing the computer to execute the functions/processing of the present invention.

In addition, it suffices to encrypt the programs of the present invention, store the encrypted data in storage media such as CD-ROMs, distribute them to users. The present invention can also be implemented by allowing users who satisfy a predetermined condition to download key information for decryption from a homepage through the Internet, executing the encrypted programs using the key information, and allowing a computer to install the programs.

The functions of the above embodiments are implemented when the OS running on the computer performs part or all of actual processing based on the instructions of the programs.

The present invention also incorporates a case wherein the programs according to the present invention are written in the memory of a function expansion unit of a PC, and the CPU of the function expansion unit or the like performs part or all of actual processing based on the programs.

According to the present invention, there can be provided an X-ray imaging system, a control method therefor, a control program, and An X-ray imaging apparatus which can perform control suitable for the currently attached X-ray sensing unit.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2006-110102 filed on Apr. 12, 2006, which is hereby incorporated by reference herein in its entirety.

What is claimed is:

1. An X-ray imaging system which allows interchangeable connection of an X-ray sensing unit, comprising:
    an X-ray generation unit adapted to apply X-rays to the X-ray sensing unit;
    an imaging controller adapted to control imaging of the X-ray sensing unit and control said X-ray generation unit;
    a receiver adapted to receive sensing unit information from the X-ray sensing unit if connection state of the X-ray sensing unit is switched from undetected state to detected state; and
    a parameter setting unit adapted to set a control parameter for said imaging controller on the basis of the sensing unit information received by said receiver to receive sensing unit information, the control parameter being adjustable by a user operation.

2. The system according to claim 1, further comprising:
    a driver module searching unit adapted to search the external network for a latest driver module;
    a driver module receiver adapted to download a driver module searched out by said driver module searching unit from the external network; and
    an imaging controller updating unit adapted to incorporate the driver module received by said driver module receiver in said imaging controller and update said imaging controller unit.

3. The system according to claim 2, wherein said driver module searching unit searches a connected X-ray sensing unit as well as the external network for a driver module.

4. The system according to claim 1, wherein the X-ray sensing unit is wirelessly connected.

5. An X-ray imaging apparatus which allows interchangeable connection of an X-ray sensing unit, comprising:
    an imaging controller adapted to control imaging of the X-ray sensing unit;
    a sensing unit information receiver adapted to receive sensing unit information from the X-ray sensing unit if connection state of the X-ray sensing unit is switched from undetected state to detected state; and
    a parameter setting unit adapted to set a control parameter for said imaging controller on the basis of the sensing unit information received by said sensing unit information receiver.

6. A control method for an X-ray imaging system which allows interchangeable connection of an X-ray sensing unit, comprising the steps of:
    receiving sensing unit information from the connected X-ray sensing unit if connection state of the X-ray sensing unit is switched from undetected state to detected state; and
    setting a control parameter for an imaging controller on the basis of the sensing unit information received in the step of receiving the sensing unit information, the imaging controller being adjustable by a user operation.

7. A control method for an X-ray imaging system which allows interchangeable connection of an X-ray sensing unit and includes an imaging controller, comprising the steps of:
    receiving a driver module for controlling a function of the X-ray sensing unit from the X-ray sensing unit if connection state of the X-ray sensing unit is switched from undetected state to detected state; and
    updating the imaging controller by using the driver module received in the step of receiving the driver module;
    a display unit to display a graphical user interface representing a control parameter which can be adjusted by a user operation; and
    a changing unit to change the display of the graphical user interface after completion of updating said imaging controller.

8. A control method for an X-ray imaging system which allows interchangeable connection of an X-ray sensing unit and includes an imaging controller, comprising the steps of:
    receiving a driver module for controlling a function of the X-ray sensing unit from an external network if connection state of the X-ray sensing unit is switched from undetected state to detected state;
    updating the imaging controller by using the driver module received in the step of receiving the driver module;
    displaying a graphical user interface representing a control parameter which can be adjusted by a user operation; and
    changing the displayed graphical user interface after completion of updating said imaging controller.

9. An X-ray imaging system which allows interchangeable connection of an X-ray sensing unit, comprising:
    an X-ray generation unit adapted to apply X-rays to the X-ray sensing unit;
    an imaging controller adapted to control imaging of the X-ray sensing unit and control said X-ray generation unit;
    a receiver adapted to receive sensing unit information from the X-ray sensing unit if connection state of the X-ray sensing unit is switched from undetected state to detected state; and
    a parameter setting unit adapted to set a control parameter for said imaging controller on the basis of the sensing unit information received by said receiver to receive sensing unit information.

10. The system according to claim 9, further comprising:
    a driver module searching unit adapted to search the external network for a latest driver module;

a driver module receiver adapted to download a driver module searched out by said driver module searching unit from the external network; and an imaging controller updating unit adapted to incorporate the driver module received by said driver module receiver in said imaging controller and update said imaging controller unit.

11. The system according to claim 10, wherein said driver module searching unit searches a connected X-ray sensing unit as well as the external network for a driver module.

12. The system according to claim 9, wherein the X-ray sensing unit is wirelessly connected.

13. A control method for an X-ray imaging system which allows interchangeable connection of an X-ray sensing unit, comprising the steps of:

receiving sensing unit information from the connected X-ray sensing unit if connection state of the X-ray sensing unit is switched from undetected state to detected state; and setting a control parameter for an imaging controller on the basis of the sensing unit information received in the step of receiving the sensing unit information.

* * * * *